(12) United States Patent
Ogawa et al.

(10) Patent No.: US 9,768,619 B2
(45) Date of Patent: Sep. 19, 2017

(54) POWER SUPPLY CONTROL CIRCUIT (71) Applicant: OLYMPUS CORPORATION, Tokyo (JP)

(72) Inventors: Keisuke Ogawa, Hino (JP); Fumiyuki Okawa, Tama (JP); Tomoharu Ogihara, Higashimurayama (JP)

(73) Assignee: OLYMPOS CORPORATION, Tokyo (JP)

( * ) Notice: Subject to any disclaimer, the term of this patent is extended or adjusted under 35 U.S.C. 154(b) by 0 days.

(21) Appl. No.: 15/371,352

(22) Filed: Dec. 7, 2016

(65) Prior Publication Data

US 2017/0085095 A1 Mar. 23, 2017

Related U.S. Application Data

(63) Continuation of application No. PCT/JP2016/054457, filed on Feb. 16, 2016.

(30) Foreign Application Priority Data

Jul. 6, 2015 (JP) ................................. 2015-135475

(51) Int. Cl.
*H02J 4/00* (2006.01)
*A61B 1/00* (2006.01)
(Continued)

(52) U.S. Cl.
CPC ............ *H02J 4/00* (2013.01); *A61B 1/00006* (2013.01); *A61B 1/00009* (2013.01);
(Continued)

(58) Field of Classification Search
CPC ............ A61B 1/00006; A61B 1/00009; A61B 1/00027; A61B 1/00045; A61B 1/04; A61B 1/045; G02B 23/24; H02J 1/00; H02J 4/00
See application file for complete search history.

(56) References Cited

U.S. PATENT DOCUMENTS

2012/0178992 A1\* 7/2012 Fujimoto ........... A61B 1/00006
600/109

FOREIGN PATENT DOCUMENTS

| JP | H05-204496 A | 8/1993 |
|---|---|---|
| JP | 2004-159812 A | 6/2004 |
| WO | WO 2012/008259 A1 | 1/2012 |

\* cited by examiner

*Primary Examiner* — Rexford Barnie
*Assistant Examiner* — Toan Vu
(74) *Attorney, Agent, or Firm* — Scully, Scott, Murphy & Presser, P.C.

(57) ABSTRACT

A power supply control circuit includes a drive voltage generation circuit configured to generate a plurality of drive voltages by using a plurality of power supply voltages that are supplied from outside, a sequencer configured to stop, when supply of the plurality of power supply voltages is stopped in a predetermined order, generation of the plurality of drive voltages according to priority ranks set in advance, and a power supply monitor circuit configured to perform, when supply of one power supply voltage, among the plurality of power supply voltages, is stopped in an order different from the predetermined order but supply of other power supply voltages is continued, an operation for simultaneously stopping generation of drive voltages that are set at higher priority ranks than a priority rank for stopping generation of a drive voltage that uses the one power supply voltage.

4 Claims, 5 Drawing Sheets

(51) Int. Cl.
*A61B 1/04* (2006.01)
*G02B 23/24* (2006.01)
*H02J 1/00* (2006.01)
*A61B 1/045* (2006.01)
*A61B 1/06* (2006.01)

(52) U.S. Cl.
CPC ...... *A61B 1/00027* (2013.01); *A61B 1/00045* (2013.01); *A61B 1/04* (2013.01); *A61B 1/045* (2013.01); *G02B 23/24* (2013.01); *H02J 1/00* (2013.01); *A61B 1/06* (2013.01)

POWER SUPPLY CONTROL CIRCUIT

CROSS REFERENCE TO RELATED APPLICATION

This application is a continuation application of PCT/JP2016/054457 filed on Feb. 16, 2016 and claims benefit of Japanese Application No. 2015-135475 filed in Japan on Jul. 6, 2015, the entire contents of which are incorporated herein by this reference.

BACKGROUND OF THE INVENTION

1. Field of the Invention

The present invention relates to a power supply control circuit, and more particularly, to a power supply control circuit configured to perform control according to supply states of a plurality of power supply voltages.

2. Description of the Related Art

Conventionally, a technology for performing sequence control according to supply states of a plurality of power supply voltages is known.

More specifically, for example, Japanese Patent Application Laid-Open Publication No. 05-204496 discloses a power supply control system that disconnects power according to a disconnection sequence set in advance such that, at the time of disconnection of power of a plurality of power supply units, power is disconnected in the order from a power supply unit, among the plurality of power supply units, with high output potential to one with low output potential. Also, Japanese Patent Application Laid-Open Publication No. 05-204496 discloses a configuration for disconnecting, according to the disconnection sequence described above, at a time of occurrence of power failure such as low voltage or overvoltage, power of a power supply unit with lower output potential than the power supply unit which is the occurrence source of the power failure.

SUMMARY OF THE INVENTION

A power supply control circuit according to an aspect of the present invention is a power supply control circuit provided to a predetermined device including a plurality of electronic components that are driven by at least one drive voltage among a plurality of drive voltages, the power supply control circuit including a drive voltage generation circuit configured to generate the plurality of drive voltages by using a plurality of power supply voltages that are supplied from outside the predetermined device, a sequencer configured to perform, when supply of the plurality of power supply voltages is stopped in a predetermined order, sequence control for stopping generation of the plurality of drive voltages by the drive voltage generation circuit according to priority ranks set in advance, and a power supply monitor circuit configured to monitor supply states of the plurality of power supply voltages to perform, in an event of occurrence of a state where supply of one power supply voltage, among the plurality of power supply voltages, is stopped in an order different from the predetermined order but supply of other power supply voltages excluding the one power supply voltage is continued, an operation for simultaneously stopping generation of drive voltages that are set at higher priority ranks than a priority rank for stopping generation of a drive voltage that uses the one power supply voltage in the sequence control.

DETAILED DESCRIPTION OF THE PREFERRED EMBODIMENT

Hereinafter, an embodiment of the present invention will be described with reference to the drawings.

FIGS. 1 to 5 are related to the embodiment of the present invention.

Figure 1:
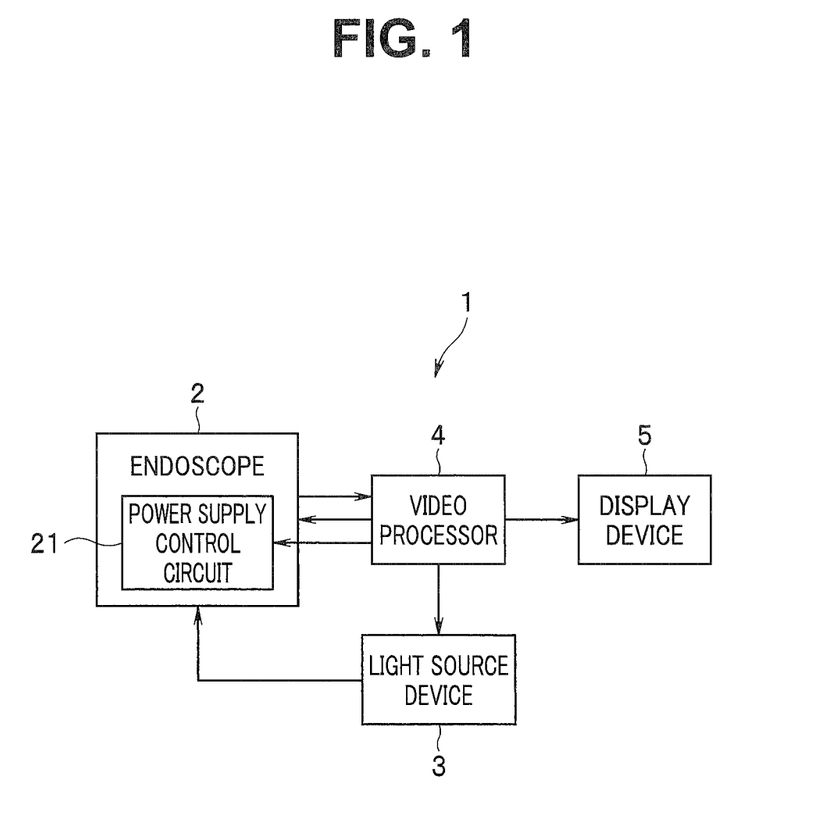
FIG. 1 is a diagram showing an example of a configuration of an endoscope system including a power supply control circuit according to an embodiment.

As shown in FIG. 1, an endoscope system 1 includes an endoscope 2 configured to be able to pick up an image of an object, such as a body tissue, present in a body cavity of a subject and to output an image pickup signal, a light source device 3 configured to be able to supply illumination light for illuminating the object to the endoscope 2, a video processor 4 configured to be able to generate and output an observation image according to the image pickup signal that is outputted from the endoscope 2, and a display device 5 configured to be able to display the observation image that is outputted from the video processor 4 or the like.

The endoscope 2 is configured to be able to perform an image pickup operation and the like according to the control of the video processor 4. Also, the endoscope 2 is provided with a power supply control circuit 21 that is configured to generate a plurality of drive voltages for driving a plurality of electronic components, such as a CCD, by using a plurality of power supply voltages supplied by the video processor 4, and to monitor and control supply states of the plurality of power supply voltages. That is, the endoscope 2 is provided with a plurality of electronic components, such as a CCD, that are driven by at least one drive voltage among the plurality of drive voltages generated by the power supply control circuit 21. Note that a specific configuration of the power supply control circuit 21 will be described later.

The light source device 3 is configured to be able to supply or to stop supplying illumination light to the endoscope 2, and to change the amount of the illumination light, under the control of the video processor 4.

The video processor 4 is configured to be able to control each of the endoscope 2 and the light source device 3.

For example, the video processor 4 is configured to be able to generate a plurality of power supply voltages VPA, VPB, and VPC different from one another by using a predetermined power supply voltage that is supplied by a commercial power supply or the like, and to supply the generated power supply voltages VPA, VPB, and VPC to the endoscope 2.

Now, a specific configuration of the power supply control circuit 21 will be described by referring to FIG. 2 as appropriate.

The power supply control circuit 21 is configured to generate a plurality of drive voltages VPX, VPY, and VPZ different from one another by using the power supply voltages VPA, VPB, and VPC that are supplied by the video processor 4. More specifically, the power supply control circuit 21 is configured to generate the drive voltage VPX by using the power supply voltage VPA supplied by the video processor 4, to generate the drive voltage VPY by using the power supply voltage VPB supplied by the video processor 4, and to generate the drive voltage VPZ by using the power supply voltage VPC supplied by the video processor 4.

The power supply control circuit 21 is configured such that, when supply of the power supply voltages VPA, VPB, and VPC is started in the following order of VPA, VPB, VPC, that is, when supply of the power supply voltages VPA, VPB, and VPC is normally started, generation of the drive voltages is started, by operation of a sequencer 31 described later, according to priority ranks set in advance in the following order of the drive voltages VPX, VPY, VPZ. The power supply control circuit 21 is also configured such that, when supply of the power supply voltages VPA, VPB, and VPC is stopped in the following order of VPC, VPB, VPA, that is, when supply of the power supply voltages VPA, VPB, and VPC is normally stopped, generation of the drive voltages is stopped and stop of supply of the power supply voltage VPC is detected by operation of the sequencer 31 described later, according to priority ranks set in advance in the following order of the drive voltages VPZ, VPY, VPX.

Figure 2:
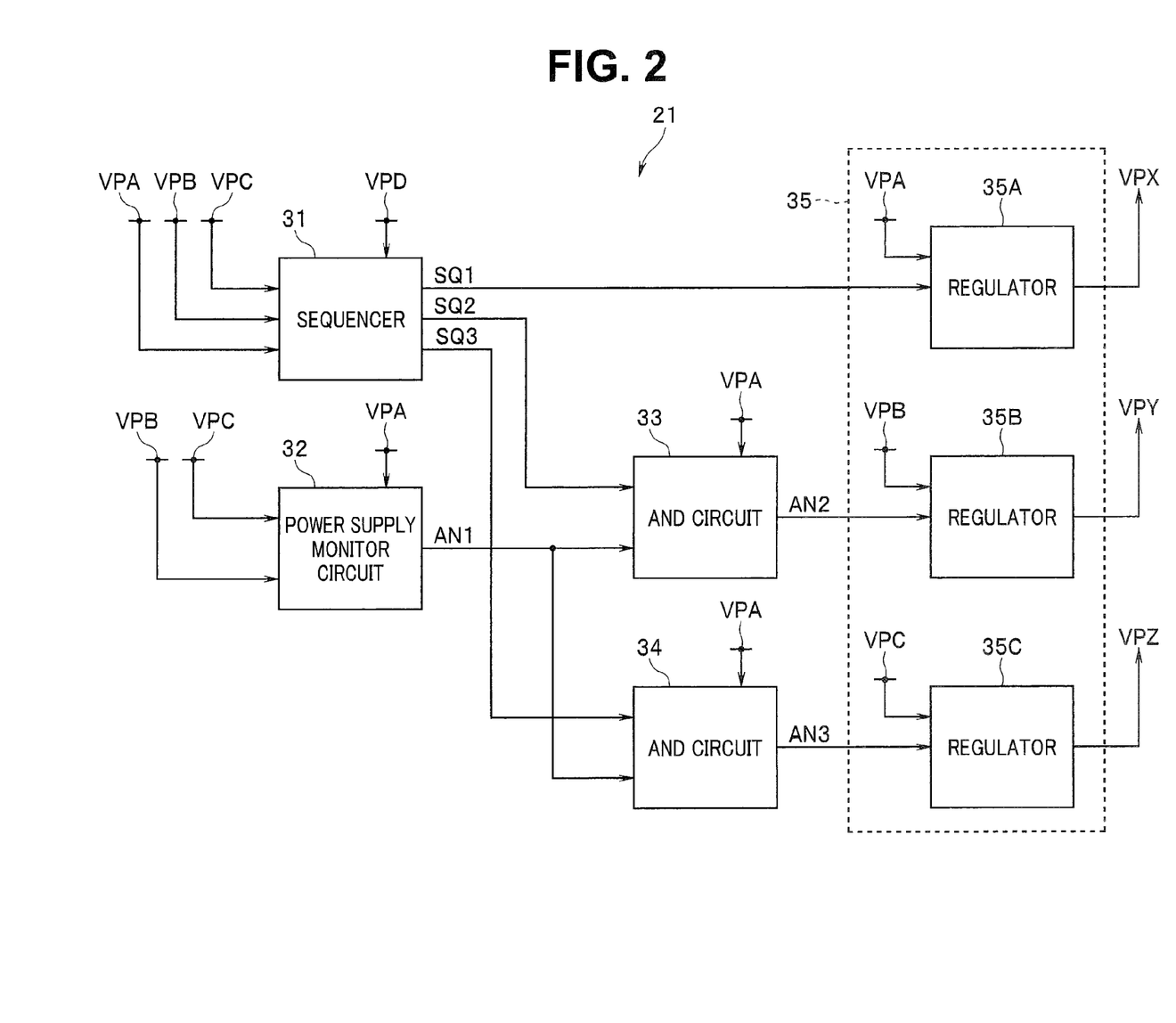
FIG. 2 is a diagram showing an example of a specific configuration of the power supply control circuit according to the embodiment.

As shown in FIG. 2, the power supply control circuit 21 is configured by including a sequencer 31, a power supply monitor circuit 32, AND circuits 33 and 34, and a drive voltage generation circuit 35, for example.

FIG. 2 is a diagram showing an example of a specific configuration of the power supply control circuit according to the embodiment.

The sequencer 31 is configured to be driven by a power supply voltage VPD different from any of the power supply voltages VPA, VPB, and VPC.

Note that the power supply voltage VPD mentioned above is a voltage at a constant voltage level supplied by a power supply outside supply routes of the power supply voltage VPA, VPB, and VPC, such as a secondary battery embedded in the endoscope 2, for example. Also, the power supply voltage VPD mentioned above is a voltage that is obtained by stabilizing the power supply voltage VPA by a stabilizer circuit or the like, and is a voltage which can maintain, for a constant time period, a voltage level which does not interfere with driving of the sequencer 31 even if supply of the power supply voltage VPA is stopped. Accordingly, in the following, description will be given by citing, as an example, a case where the sequencer 31 is driven at all times regardless of a change in the supply states of the power supply voltages VPA, VPB, and VPC.

The sequencer 31 is configured to output, as output signals according to the supply states of the power supply voltages VPA, VPB, and VPC, an output signal SQ1 to a regulator 35A, an output signal SQ2 to the AND circuit 33, and an output signal SQ3 to the AND circuit 34.

More specifically, the sequencer 31 is configured to output, during a period when the three power supply voltages of the power supply voltages VPA, VPB, and VPC are not supplied, each of the output signals SQ1, SQ2, and SQ3 at a Low level (hereinafter referred to also as "L level").

Furthermore, the sequencer 31 is configured to perform, when start of supply of the three power supply voltages of the power supply voltages VPA, VPB, and VPC is detected, an operation for shifting the signal levels of respective output signals from the Low level to a High level (hereinafter referred to also as a "H level") in the following order of SQ1, SQ2, SQ3. That is, the sequencer 31 is configured to perform sequence control of starting, when supply of all the power supply voltages VPA, VPB, and VPC is started, generation of drive voltages by the drive voltage generation circuit 35 according to the priority ranks set in advance in the following order of the drive voltages VPX, VPY, VPZ.

Furthermore, the sequencer 31 is configured to output, during a period when the three power supply voltages of the power supply voltages VPA, VPB, and VPC are being supplied, each of the output signals SQ1, SQ2, and SQ3 at the High level.

Moreover, the sequencer 31 is configured to perform, when stop of supply of one power supply voltage among the power supply voltages VPA, VPB, and VPC is detected, an operation for shifting the signal levels of respective output signals from the High level to the Low level in the following order of SQ3, SQ2, SQ1. That is, the sequencer 31 is configured to perform sequence control of stopping, when supply of one power supply voltage among the power supply voltages VPA, VPB, and VPC is stopped, generation of drive voltages by the drive voltage generation circuit 35 according to the priority ranks set in advance in the following order of the drive voltages VPZ, VPY, VPX.

The power supply monitor circuit 32 is provided with an AND circuit or the like, and is configured to be driven by the power supply voltage VPA supplied by the video processor 4, for example. That is, the power supply monitor circuit 32 is configured to be driven by the power supply voltage VPA, which is used for generation of the drive voltage VPX set at the lowest priority rank with respect to the sequence control to be performed by the sequencer 31 when supply of one power supply voltage among the power supply voltages VPA, VPB, and VPC is stopped.

The power supply monitor circuit 32 is configured to monitor the supply states of the three power supply voltages of the power supply voltages VPA, VPB, and VPC to thereby output a High level output signal AN1 in a case where the supply states of all the three power supply voltages are normal. Also, the power supply monitor circuit 32 is configured to monitor the supply states of the three power supply voltages of the power supply voltages VPA, VPB, and VPC to thereby output a Low level output signal AN1 in a case where there is an abnormality in the supply state of at least one of the three power supply voltages.

The AND circuit 33 is configured to be driven by the power supply voltage VPA supplied by the video processor 4.

The AND circuit 33 is configured to output a Low level output signal AN2 to a regulator 35B in a case where the signal level of at least one of the output signals SQ2 and AN1 is at the Low level.

The AND circuit 33 is configured to output a High level output signal AN2 to the regulator 35B in a case where the signal levels of both the output signals SQ2 and AN1 are at the High level.

The AND circuit 34 is configured to output a Low level output signal AN3 to a regulator 35C in a case where the signal level of at least one of the output signals SQ3 and AN1 is at the Low level.

The AND circuit 34 is configured to output a High level output signal AN3 to the regulator 35C in a case where the signal levels of both the output signals SQ3 and AN1 are at the High level.

The drive voltage generation circuit 35 is configured to perform an operation for generating the plurality of drive voltages VPX, VPY, and VPZ by using the plurality of power supply voltages VPA, VPB, and VPC supplied by the video processor 4, according to the signal levels of the output signals SQ1, AN2, and AN3. Also, the drive voltage generation circuit 35 is configured by including the regulator 35A that performs an operation according to the signal level of the output signal SQ1, the regulator 35B that performs an operation according to the signal level of the output signal AN2, and the regulator 35C that performs an operation according to the signal level of the output signal AN3.

The regulator 35A is configured to perform an operation for generating the drive voltage VPX by using the power supply voltage VPA, during a period when a High level output signal SQ1 is being inputted.

The regulator 35A is configured to stop the operation for generating the drive voltage VPX by using the power supply voltage VPA, during a period when a Low level output signal SQ1 is being inputted.

The regulator 35B is configured to perform an operation for generating the drive voltage VPY by using the power supply voltage VPB, during a period when a High level output signal AN2 is being inputted.

The regulator 35B is configured to stop the operation for generating the drive voltage VPY by using the power supply voltage VPB, during a period when a Low level output signal AN2 is being inputted.

The regulator 35C is configured to perform an operation for generating the drive voltage VPZ by using the power supply voltage VPC, during a period when a High level output signal AN3 is being inputted.

The regulator 35C is configured to stop the operation for generating the drive voltage VPZ by using the power supply voltage VPC, during a period when a Low level output signal AN3 is being inputted.

Note that, according to the present embodiment, the regulators 35A to 35C may be configured by other electronic circuits such as switching power supply circuits.

Subsequently, a specific operation of the power supply control circuit 21 according to the present embodiment will be described by citing, as an example, a case where the supply state of the power supply voltage from the video processor 4 to the endoscope 2 reaches an originally unintended state due to, for example, hot swapping of an electrical connection portion (not shown) for electrically connecting the endoscope 2 and the video processor 4.

Figure 3:
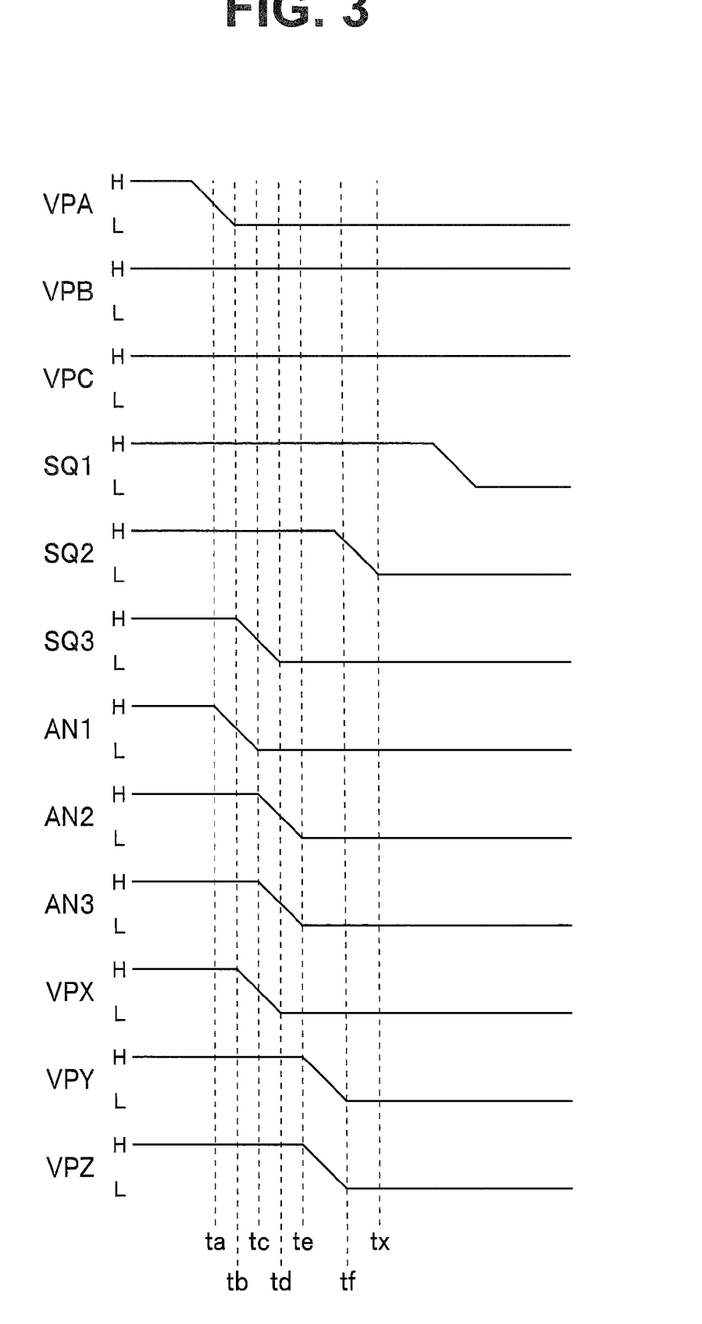
FIG. 3 is a timing chart for describing an example operation that is performed by the power supply control circuit according to the embodiment in a case where a supply state of a power supply voltage reaches an originally unintended state.

First, details of an operation of the power supply control circuit 21 in a case where only the power supply voltage VPA, among the power supply voltages VPA, VPB, and VPC, stops being supplied to the endoscope 2 will be given by referring to FIG. 3 as appropriate. FIG. 3 is a timing chart for describing an example operation that is performed by the power supply control circuit according to the embodiment in a case where the supply state of a power supply voltage reaches an originally unintended state.

For example, as shown in FIG. 3, the sequencer 31 starts an operation for shifting the output signal SQ3 from the H level to the L level at a time point tb corresponding to a timing of completion of the shift of the supply state of the power supply voltage VPA to the L level, and completes the operation for shifting the output signal SQ3 from the H level to the L level at a time point td corresponding to a timing later than the time point tb.

The regulator 35A is not able to maintain the voltage level of the drive voltage VPX at the H level after completion of the shift of the supply state of the power supply voltage VPA from the H level to the L level. Accordingly, as shown in FIG. 3, for example, the drive voltage VPX starts shifting from the H level to the L level at the time point tb, and completes the shift to the L level at the time point td.

On the other hand, the power supply monitor circuit 32 monitors the supply states of the power supply voltages VPA, VPB, and VPC so that, in the event of occurrence of a state where supply of the power supply voltage WA is stopped but supply of the power supply voltages VPB and VPC is continued, an operation is performed to simultaneously stop generation of the drive voltages VPY and VPZ which are set at higher priority ranks than the priority rank for stopping generation of the drive voltage VPX that uses the power supply voltage WA in the sequence control by the sequencer 31.

Here, as the supply state of the power supply voltage WA shifts from the H level to the L level, the power supply monitor circuit 32 is disabled from maintaining the signal level of the output signal AN1 at the H level regardless of input of the H level power supply voltages VPB and VPC. Accordingly, as shown in FIG. 3, for example, the output signal AN1 starts shifting from the H level to the L level at a time point to corresponding to a timing before the time point tb, which is during shifting of the supply state of the power supply voltage VPA from the H level to the L level, and completes the shift to the L level at a time point tc corresponding to a timing later than the time point tb and before the time point td. That is, according to the operation of the power supply monitor circuit 32 as described above, the L level output signal AN1 indicating occurrence of an abnormality in the supply state of the power supply voltage VPA may be outputted at the time point tc.

The AND circuit 33 is not able to maintain the signal level of the output signal AN2 at the H level after completion of the shift of the supply state of the power supply voltage VPA to the L level. Accordingly, as shown in FIG. 3, for example, the output signal AN2 starts shifting from the H level to the L level at the time point tc of input of the L level output signal AN1, and completes the shift to the L level at a time point te corresponding to a timing later than the time point td.

The AND circuit 34 is not able to maintain the signal level of the output signal AN3 at the H level after completion of the shift of the supply state of the power supply voltage VPA to the L level. Accordingly, as shown in FIG. 3, for example, the output signal AN3 starts shifting from the H level to the L level at the time point tc of input of the L level output signal AN1, and completes the shift to the L level at the time point te.

As shown in FIG. 3, for example, the regulator 35B starts an operation for shifting the drive voltage VPY from the H level to the L level at the time point te of input of the L level output signal AN2, and completes the operation for shifting the drive voltage VPY from the H level to the L level at a time point tf corresponding to a timing later than the time point te. That is, according to the operation illustrated in FIG. 3, the regulator 35B starts the operation for stopping generation of the drive voltage VPY at the time point te, and completes the operation for stopping generation of the drive voltage VPY at the time point tf.

For example, as shown in FIG. 3, the regulator 35C starts an operation for shifting the drive voltage VPZ from the H level to the L level at the time point te of input of the L level output signal AN3, and completes the operation for shifting the drive voltage VPZ from the H level to the L level at the time point tf. That is, according to the operation illustrated in FIG. 3, the regulator 35C starts the operation for stopping generation of the drive voltage VPZ at the time point te, and completes the operation for stopping generation of the drive voltage VPZ at the time point tf.

For example, in the case of a circuit configuration where the output signal SQ1 is directly inputted to the regulator 35A, the output signal SQ2 is directly inputted to the regulator 35B, and the output signal SQ3 is directly inputted to the regulator 35C, generation of the drive voltage VPY cannot be stopped before a timing indicated as a time point tx in FIG. 3, that is, a timing of completion of the shift of the signal level of the output signal SQ2 to the L level. Accordingly, with the circuit configuration as described above, if only the power supply voltage VPA among the power supply voltages VPA, VPB, and VPC, stops being supplied to the endoscope 2, an inconvenience such as a latch-up becomes highly likely to occur at an electronic component which is the supply destination of the drive voltage VPY.

On the other hand, according to the operation of the power supply control circuit 21 as illustrated in FIG. 3, in the event of occurrence of an abnormality in the supply state of a power supply voltage, as in the case where supply of the power supply voltage VPA is stopped but supply of the power supply voltages VPB and VPC is continued, generation of the drive voltages VPY and VPZ may be simultaneously stopped at the time point tf corresponding to a timing before completion of the shift of the signal level of the output signal SQ2 to the L level. Therefore, according to the operation of the power supply control circuit 21 as illustrated in FIG. 3, the possibility of an inconvenience such as a latch-up occurring at electronic components which are supply destinations of the drive voltages VPY and VPZ in the event of occurrence of an abnormality such as supply of only the power supply voltage VPA, among the power supply voltages VPA, VPB, and VPC, to the endoscope 2 being stopped may be reduced as much as possible.

Figure 4:
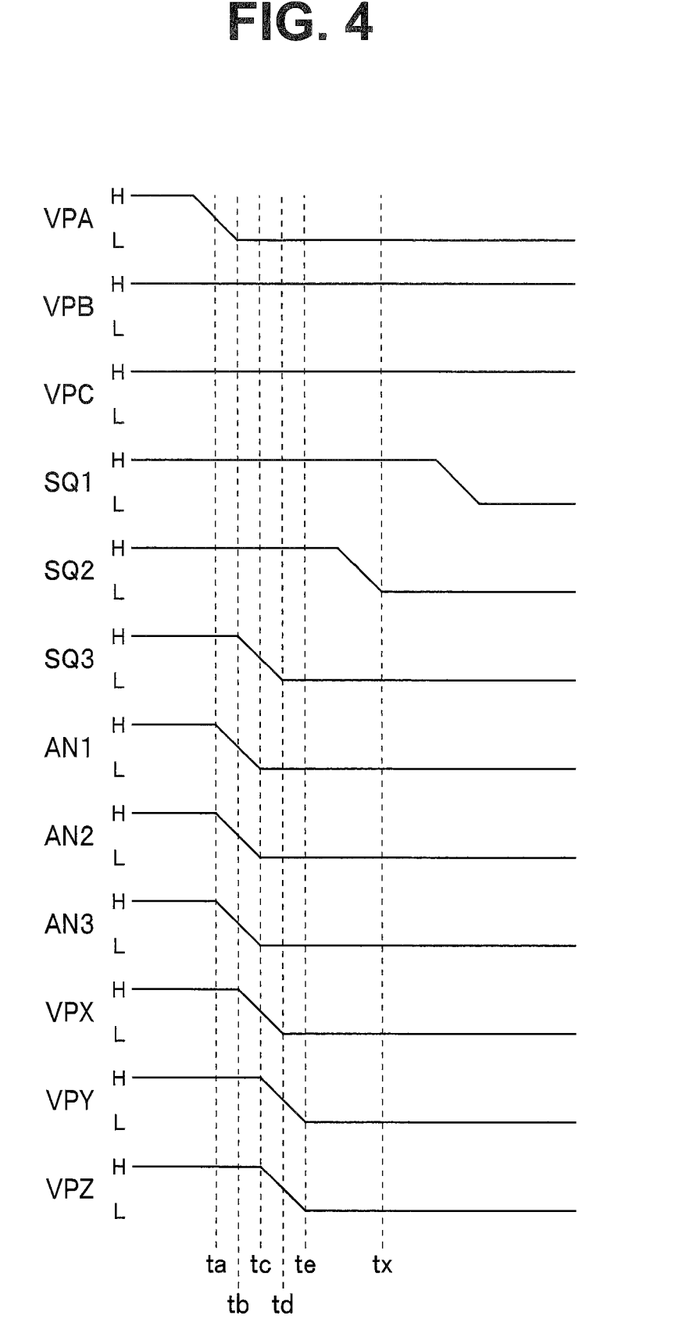
FIG. 4 is a timing chart for describing an example operation that is performed by the power supply control circuit according to the embodiment in a case where a supply state of a power supply voltage reaches an originally unintended state.

Now, according to the present embodiment, in a case where only the power supply voltage VPA, among the power supply voltages VPA, VPB, and VPC, stops being supplied to the endoscope 2, an operation as shown in FIG. 4 may be performed by the power supply control circuit 21, without being limited to the operation by the power supply control circuit 21 as shown in FIG. 3, for example. Details of such an operation will be given below. FIG. 4 is a timing chart for describing an example operation that is performed by the power supply control circuit according to the embodiment in a case where the supply state of a power supply voltage reaches an originally unintended state. Note that, in the following, specific description of components and the like described above will be omitted as appropriate for the sake of simplicity.

As shown in FIG. 4, for example, the sequencer 31 starts an operation for shifting the output signal SQ3 from the H level to the L level at the time point tb, and completes the operation for shifting the output signal SQ3 from the H level to the L level at the time point td.

The regulator 35A is not able to maintain the voltage level of the drive voltage VPX at the H level after completion of the shift of the supply state of the power supply voltage VPA from the H level to the L level. Accordingly, as shown in FIG. 4, for example, the drive voltage VPX starts shifting from the H level to the L level at the time point tb, and ends the shift to the L level at the time point td.

As the supply state of the power supply voltage VPA shifts from the H level to the L level, the power supply monitor circuit 32 is disabled from maintaining the signal level of the output signal AN1 at the H level regardless of input of the H level power supply voltages VPB and VPC. Accordingly, as shown in FIG. 4, for example, the output signal AN1 starts shifting from the H level to the L level at the time point ta, and completes the shift to the L level at the time point tc.

As the supply state of the power supply voltage VPA shifts from the H level to the L level, the AND circuit 33 is disabled from maintaining the signal level of the output signal AN2 at the H level (regardless of input of the H level output signals SQ2 and AN1). Accordingly, as shown in FIG. 4, for example, the output signal AN2 starts shifting from the H level to the L level at the time point ta, and completes the shift to the L level at the time point tc.

As the supply state of the power supply voltage VPA shifts from the H level to the L level, the AND circuit 34 is disabled from maintaining the signal level of the output signal AN3 at the H level (regardless of input of the H level output signals SQ3 and AN1). Accordingly, as shown in FIG. 4, for example, the output signal AN3 starts shifting from the H level to the L level at the time point ta, and completes the shift to the L level at the time point tc.

As shown in FIG. 4, for example, the regulator 35B starts an operation for shifting the drive voltage VPY from the H level to the L level at the time point tc of input of the L level output signal AN2, and completes the operation for shifting the drive voltage VPY from the H level to the L level at the time point te. That is, according to the operation illustrated in FIG. 4, the regulator 35B starts the operation for stopping generation of the drive voltage VPY at the time point tc, and completes the operation for stopping generation of the drive voltage VPY at the time point te.

As shown in FIG. 4, for example, the regulator 35C starts an operation for shifting the drive voltage VPZ from the H level to the L level at the time point tc of input of the L level output signal AN3, and completes the operation for shifting the drive voltage VPZ from the H level to the L level at the time point te. That is, according to the operation illustrated in FIG. 4, the regulator 35C starts the operation for stopping generation of the drive voltage VPZ at the time point tc, and completes the operation for stopping generation of the drive voltage VPZ at the time point te.

As described above, according to the operation of the power supply control circuit 21 illustrated in FIG. 4, in the event of occurrence of an abnormality in the supply state of a power supply voltage, as in the case where supply of the power supply voltage VPA is stopped but supply of the power supply voltages VPB and VPC is continued, generation of the drive voltages VPY and VPZ may be simultaneously stopped at the time point te corresponding to a timing before completion of the shift of the signal level of the output signal SQ2 to the L level. Therefore, according to the operation of the power supply control circuit 21 as illustrated in FIG. 4, the possibility of an inconvenience such as a latch-up occurring at electronic components which are supply destinations of the drive voltages VPY and VPZ in the event of occurrence of an abnormality such as supply of only the power supply voltage VPA, among the power supply voltages VPA, VPB, and VPC, to the endoscope 2 being stopped may be reduced as much as possible.

Figure 5:
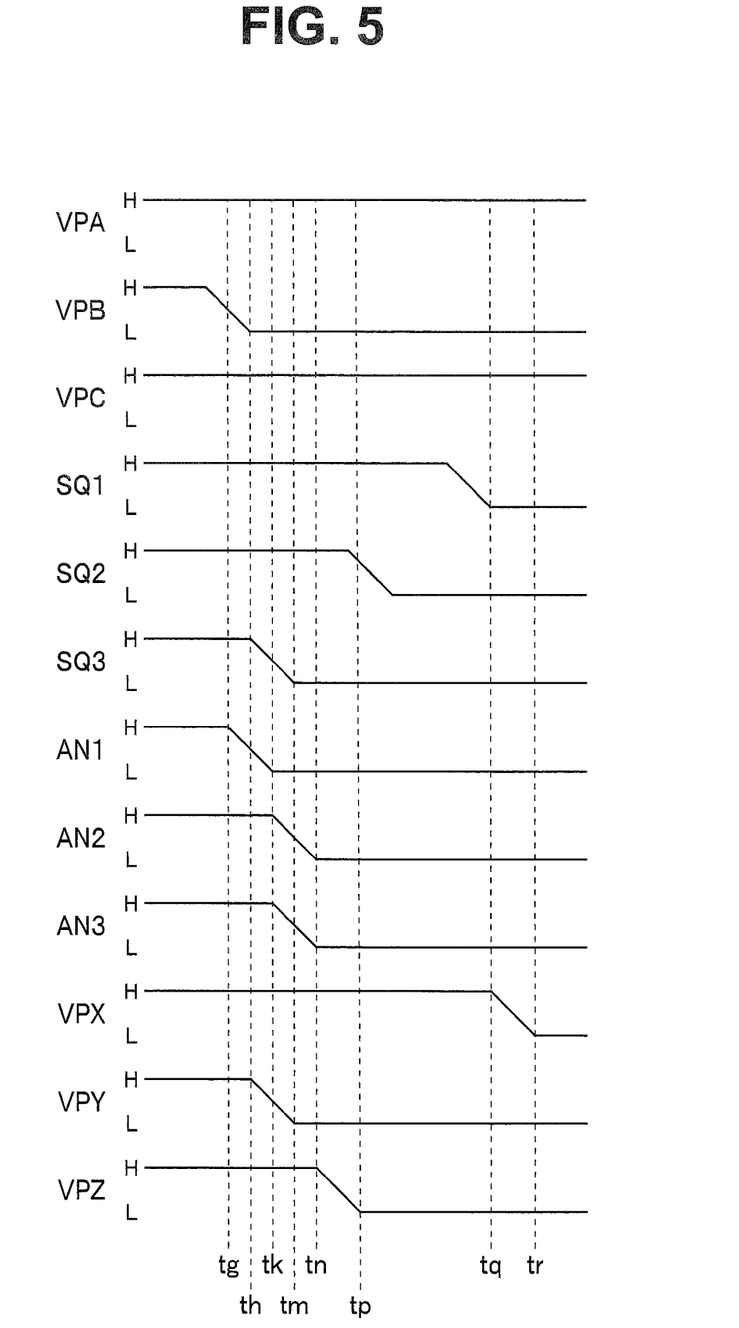
FIG. 5 is a timing chart for describing an example operation that is performed by the power supply control circuit according to the embodiment in a case where a supply state of a power supply voltage reaches an originally unintended state.

Next, details of an operation of the power supply control circuit 21 in a case where only the power supply voltage VPB, among the power supply voltages VPA, VPB, and VPC, stops being supplied to the endoscope 2 will be given by referring to FIG. 5 as appropriate. FIG. 5 is a timing chart for describing an example operation that is performed by the power supply control circuit according to the embodiment in a case where the supply state of a power supply voltage reaches an originally unintended state.

For example, as shown in FIG. 5, the sequencer 31 starts an operation for shifting the output signal SQ3 from the H level to the L level at a time point th corresponding to a timing of completion of the shift of the supply state of the power supply voltage VPB to the L level, and completes the operation for shifting the output signal SQ3 from the H level to the L level at a time point tm corresponding to a timing later than the time point th.

The regulator 35B is not able to maintain the voltage level of the drive voltage VPY at the H level after completion of the shift of the supply state of the power supply voltage VPB from the H level to the L level. Accordingly, as shown in FIG. 5, for example, the drive voltage VPY starts shifting from the H level to the L level at the time point th, and completes the shift to the L level at the time point tm.

Here, as the supply state of the power supply voltage VPB shifts from the H level to the L level, the power supply monitor circuit 32 is disabled from maintaining the signal level of the output signal AN1 at the H level. Accordingly, as shown in FIG. 5, for example, the output signal AN1 starts shifting from the H level to the L level at a time point tg corresponding to a timing before the time point th, which is during shifting of the supply state of the power supply voltage VPB from the H level to the L level, and completes the shift to the L level at a time point tk corresponding to a timing later than the time point th and before the time point tm. That is, according to the operation of the power supply monitor circuit 32 as described above, the L level output signal AN1 indicating occurrence of an abnormality in the supply state of the power supply voltage VPB may be outputted at the time point tk.

As shown in FIG. 5, for example, the AND circuit 33 starts an operation for shifting the signal level of the output signal AN2 from the H level to the L level at the time point tk of input of the L level output signal AN1, and completes the operation for shifting the signal level of the output signal AN2 from the H level to the L level at a time point tn corresponding to a timing later than the time point tm.

As shown in FIG. 5, for example, the AND circuit 34 starts an operation for shifting the signal level of the output signal AN2 from the H level to the L level at the time point tk of input of the L level output signal AN1, and completes the operation for shifting the signal level of the output signal AN2 from the H level to the L level at the time point tn.

As shown in FIG. 5, for example, the regulator 35C starts an operation for shifting the drive voltage VPZ from the H level to the L level at the time point tn of input of the L level output signal AN3, and completes the operation for shifting the drive voltage VPZ from the H level to the L level at a time point tp corresponding to a timing later than the time point tn and before the completion of the shift of the signal level of the output signal SQ2 to the L level. That is, according to the operation illustrated in FIG. 5, the regulator 35C starts the operation for stopping generation of the drive voltage VPZ at the time point tn, and completes the operation for stopping generation of the drive voltage VPZ at the time point tp.

As shown in FIG. 5, for example, the regulator 35A starts an operation for shifting the drive voltage VPX from the H level to the L level at a time point tq corresponding to a timing later than the time point tp and later than the completion of the shift of the signal level of the output signal SQ1 to the L level, and completes the operation for shifting the drive voltage VPX from the H level to the L level at a time point tr corresponding to a timing later than the time point tq.

As described above, according to the operation of the power supply control circuit 21 illustrated in FIG. 5, in the event of occurrence of an abnormality in the supply state of a power supply voltage, as in the case where supply of the power supply voltage VPB is stopped but supply of the power supply voltages VPA and VPC is continued, generation of the drive voltage VPZ may be stopped at the time point tp. Therefore, according to the operation of the power supply control circuit 21 as illustrated in FIG. 5, the possibility of an inconvenience such as a latch-up occurring at an electronic component which is a supply destination of the drive voltage VPZ in the event of occurrence of an abnormality such as supply of only the power supply voltage VPB, among the power supply voltages VPA, VPB, and VPC, to the endoscope 2 being stopped may be reduced as much as possible.

Note that, according to the present embodiment, the power supply control circuit 21 may be configured such that the order of the sizes of the time constants of the power supply voltages VPA to VPC and the drive voltages VPX to VPZ on the supply routes is set as a reverse order of the priority ranks for stopping generation of the drive voltages VPX, VPY, and VPZ, for example. More specifically, according to the present embodiment, in the case of stopping generation of the drive voltages according to the priority ranks set in advance in the following order of the drive voltages VPZ, VPY, VPX, the power supply control circuit 21 may be configured by disposing a voltage dividing resistor, a bypass capacitor and the like so that a relationship of $\tau X > \tau y > \tau Z$ is established among the time constant TX of the power supply voltage VPA and the drive voltage VPX on the supply route, the time constant $\tau y$ of the power supply voltage VPB and the drive voltage VPY on the supply route, and the time constant $\tau z$ of the power supply voltage VPC and the drive voltage VPZ on the supply route, for example. According to such a configuration, at the time of stopping generation of the drive voltages VPX, VPY, and VPZ, for example, the time required for the drive voltage VPZ to be completely shifted to the L level may be relatively reduced, and also, the time required for the drive voltage VPX to be completely shifted to the L level may be relatively increased.

The present invention is not limited to the embodiment described above, and it is needless to say that various modifications, applications and the like are possible within the scope of the invention.

What is claimed is:

1. A power supply control circuit provided to a predetermined device including a plurality of electronic components that are driven by at least one drive voltage among a plurality of drive voltages, the power supply control circuit comprising:
    a drive voltage generation circuit configured to generate the plurality of drive voltages by using a plurality of power supply voltages that are supplied from outside the predetermined device;
    a sequencer configured to perform, when supply of the plurality of power supply voltages is stopped in a predetermined order, sequence control for stopping generation of the plurality of drive voltages by the drive voltage generation circuit according to priority ranks set in advance; and a power supply monitor circuit configured to monitor supply states of the plurality of power supply voltages to perform, in an event of occurrence of a state where supply of one power supply voltage, among the plurality of power supply voltages, is stopped in an order different from the predetermined order but supply of other power supply voltages excluding the one power supply voltage is continued, an operation for simultaneously stopping generation of drive voltages that are set at higher priority ranks than a priority rank for stopping generation of a drive voltage that uses the one power supply voltage in the sequence control.

2. The power supply control circuit according to claim 1, wherein the power supply monitor circuit is configured to be driven by a power supply voltage, among the plurality of power supply voltages, that is used for generation of a drive voltage that is set at a lowest priority rank in the sequence control.

3. The power supply control circuit according to claim 1, wherein an order of sizes of time constants of the plurality of power supply voltages and the plurality of drive voltages on supply routes is set as a reverse order of the priority ranks for stopping generation of the plurality of drive voltages in the sequence control.

4. The power supply control circuit according to claim 1, wherein the sequencer controls the drive voltage generation circuit so that the plurality of drive voltages are generated in an order from a drive voltage at a low priority rank to a drive voltage at a high priority rank, among the priority ranks set in advance, and controls the drive voltage generation circuit so that generation of the plurality of drive voltages is stopped in an order from a drive voltage at a high priority rank to a drive voltage at a low priority rank, among the priority ranks set in advance.

* * * * *